United States Patent
Lex

(10) Patent No.: US 7,177,032 B2
(45) Date of Patent: Feb. 13, 2007

(54) DEVICE AND METHOD FOR DETERMINING THE PROPERTIES OF SURFACES

(75) Inventor: Konrad Lex, Königsdorf (DE)

(73) Assignee: BYK Gardner GmbH, Geretsried (DE)

( * ) Notice: Subject to any disclaimer, the term of this patent is extended or adjusted under 35 U.S.C. 154(b) by 350 days.

(21) Appl. No.: 10/854,926

(22) Filed: May 27, 2004

(65) Prior Publication Data
US 2005/0018195 A1      Jan. 27, 2005

(30) Foreign Application Priority Data
May 27, 2003   (DE)   ................ 103 24 104

(51) Int. Cl.
*G01B 11/30*   (2006.01)
(52) U.S. Cl. ............... 356/600; 356/425; 356/405; 356/406; 356/402
(58) Field of Classification Search ........... 356/600, 356/425, 402, 405, 406
See application file for complete search history.

(56) References Cited

U.S. PATENT DOCUMENTS 4,976,545 A * 12/1990 Kipphan et al. ............ 356/446
6,263,291 B1 * 7/2001 Shakespeare et al. ........ 702/85
7,006,229 B2 * 2/2006 Sperling et al. ............. 356/445

* cited by examiner

*Primary Examiner*—Gregory J. Toatley, Jr.
*Assistant Examiner*—Tri Ton
(74) *Attorney, Agent, or Firm*—Greer Burns & Crain Ltd.

(57) ABSTRACT

A method for determining the properties of surfaces wherein a first process step specified radiation emits from at least one radiation source to a measuring surface, in further process steps the radiation reflected and/or scattered off the measuring surface is detected by a plurality of image-capturing components, and a signal is generated which specifies at least one parameter of the radiation detected by the image-capturing components. In further process steps the first signals are grouped based on predetermined criteria to form group signals, and at least one group-specific evaluation figure is computed, and a dependent statistical parameter correlating with at least one measuring surface remission characteristic. Finally at least one statistical parameter is read out in dependence on the predetermined criterion for grouping said first signals. The properties of the surface are specified by a relation between at least two statistical parameters.

29 Claims, 3 Drawing Sheets

ABCDEFGHIJKLMN
BCDEFGHIJKLMNO
CDEFGHIJKLMNOP
DEFGHIJKLMNOPQ
EFGHIJKLMNOPQR
FGHIJKLMNOPQRS
GHIJKLMNOPQRST

Fig. 5a

```
ABCDEFGHIJKLMNOPQRSTUVWXYZABCDEFGHIJKLMNOPQRSTUVWXYZ
BCDEFGHIJKLMNOPQRSTUVWXYZABCDEFGHIJKLMNOPQRSTUVWXYZA
CDEFGHIJKLMNOPQRSTUVWXYZABCDEFGHIJKLMNOPQRSTUVWXYZAB
DEFGHIJKLMNOPQRSTUVWXYZABCDEFGHIJKLMNOPQRSTUVWXYZABC
EFGHIJKLMNOPQRSTUVWXYZABCDEFGHIJKLMNOPQRSTUVWXYZABCD
FGHIJKLMNOPQRSTUVWXYZABCDEFGHIJKLMNOPQRSTUVWXYZABCDE
GHIJKLMNOPQRSTUVWXYZABCDEFGHIJKLMNOPQRSTUVWXYZABCDEF
HIJKLMNOPQRSTUVWXYZABCDEFGHIJKLMNOPQRSTUVWXYZABCDEFG
IJKLMNOPQRSTUVWXYZABCDEFGHIJKLMNOPQRSTUVWXYZABCDEFGH
JKLMNOPQRSTUVWXYZABCDEFGHIJKLMNOPQRSTUVWXYZABCDEFGHI
KLMNOPQRSTUVWXYZABCDEFGHIJKLMNOPQRSTUVWXYZABCDEFGHIJ
LMNOPQRSTUVWXYZABCDEFGHIJKLMNOPQRSTUVWXYZABCDEFGHIJK
MNOPQRSTUVWXYZABCDEFGHIJKLMNOPQRSTUVWXYZABCDEFGHIJKL
NOPQRSTUVWXYZABCDEFGHIJKLMNOPQRSTUVWXYZABCDEFGHIJKLM
OPQRSTUVWXYZABCDEFGHIJKLMNOPQRSTUVWXYZABCDEFGHIJKLMN
PQRSTUVWXYZABCDEFGHIJKLMNOPQRSTUVWXYZABCDEFGHIJKLMNO
QRSTUVWXYZABCDEFGHIJKLMNOPQRSTUVWXYZABCDEFGHIJKLMNOP
RSTUVWXYZABCDEFGHIJKLMNOPQRSTUVWXYZABCDEFGHIJKLMNOPQ
STUVWXYZABCDEFGHIJKLMNOPQRSTUVWXYZABCDEFGHIJKLMNOPQR
TUVWXYZABCDEFGHIJKLMNOPQRSTUVWXYZABCDEFGHIJKLMNOPQRS
UVWXYZABCDEFGHIJKLMNOPQRSTUVWXYZABCDEFGHIJKLMNOPQRST
VWXYZABCDEFGHIJKLMNOPQRSTUVWXYZABCDEFGHIJKLMNOPQRSTU
WXYZABCDEFGHIJKLMNOPQRSTUVWXYZABCDEFGHIJKLMNOPQRSTUV
XYZABCDEFGHIJKLMNOPQRSTUVWXYZABCDEFGHIJKLMNOPQRSTUVW
YZABCDEFGHIJKLMNOPQRSTUVWXYZABCDEFGHIJKLMNOPQRSTUVWX
ZABCDEFGHIJKLMNOPQRSTUVWXYZABCDEFGHIJKLMNOPQRSTUVWXY
```

DEVICE AND METHOD FOR DETERMINING THE PROPERTIES OF SURFACES

FIELD OF THE INVENTION

The present invention relates to a device and a method for determining the properties of surfaces.

BACKGROUND OF THE INVENTION

The quality of surfaces is a significant property of objects used in everyday life such as motor vehicles or other consumer items, thus decisively determining their overall impression on a human observer. Examples therefor are high-gloss or metallic finishes of car bodies.

The reproducible evaluation of the quality of surfaces in particular of said high-gloss finishes requires measuring instruments which capture precisely those physical quantities which decisively determine the overall impression on a human observer. Various methods and devices are known in the prior art for determining the visual properties and specifically the reflection and diffusion characteristics of surfaces.

There is the problem that the optical impression of surfaces on a human observer also depends on the resolution capability of the human eye which in turn depends on the distance of the observer from the object, for example a vehicle.

At short distances, the human eye is capable of precisely resolving for example different color contrasts. At longer distances for instance periodic patterns will be better recognizable. The visibility of e.g. periodic textures to the human eye depends on the wavelength or frequency of the texture and on the distance of the eye from the observed object.

SUMMARY OF THE INVENTION

It is therefore the object of the present invention to provide a method and a device which allows an evaluation of surface properties where in particular such impressions are included or to be simulated which result from different distances of an observer from the observed surface.

According to the invention this object is fulfilled by the method of claim 1 and the device of claim 11. Advantageous enhancements to the method and the device are the objects of the subclaims.

The method of the invention is firstly, to emit specified radiation from at least one radiation means to a measuring surface at a specified angle. The radiation reflected and/or scattered off the measuring surface is determined by means of a detector means having a plurality of image-capturing components.

Further, a plurality of signals is generated which specify at least one parameter of the radiation detected by the image-capturing component. Finally, the first signals are grouped based on at least two different predetermined criteria to form at least two group signals, at least one group-specific evaluation figure is computed, and at least one statistical parameter dependent thereon and correlating with at least one remission characteristic of the measuring surface is specified. Finally the at least one statistical parameter is read out in dependence on the predetermined criterion for grouping said first signals. The properties of the surface are specified by means of a relation between at least two statistical parameters based on different criteria.

Radiation in this context is understood to mean radiation in the range visible to the human eye but may also include ultraviolet, infrared, X-radiation or the like. Radiation in a wavelength range visible to the human eye is, however, preferred. The radiation may be monochromatic or a composition of portions having different wavelengths.

Measuring surface is understood to mean the surface to be examined, for example a car body or the marble effect of plastics or generally of any industrially manufactured material.

Image-capturing components are preferably understood to mean electronic devices which capture radiation and react to changes of the characteristics of said radiation in a specified way.

Although the measuring surface may be an even or uneven plane, even planes will primarily be discussed within the scope of the present invention.

The properties of surfaces within the scope of the invention are understood to mean in particular those physical properties of a surface which are decisive for the appearance of the surface to a human observer. These include above all properties such as macro- and microtexture, topography, color, color location, color brightness, gloss, distinctness of image, haze, finish texture, roughness and orange peel. Within the scope of the present invention, particular attention will be paid to the properties "coarseness" or "grain".

It is preferred that the first signal depend on the intensity of the radiation impinging on the respective image-capturing components.

It is preferred that for grouping said first signals to form a group signal, at least one first signal be weighted differently from at least one other first signal. This way allows that for example existing brightness differences or contrasts can be illustrated at increased intensity or amplification. Alternatively, a plurality of first signals may be repeatedly grouped to form a group signal which also results in amplification of existing contrasts.

It is preferred that the criteria applied for grouping the first signals to form a group signal differ substantially in the number and/or the weighting and/or the function of the grouped first signals. As explained above, a weighting of the first signals may serve to amplify an impression of an existing contrast.

The number of the grouped signals may serve to vary the image resolution such as to simulate at least partially a longer or shorter distance of a human observer from the measuring surface.

It is preferred that the relationship of the at least two parameters is selected from a group of parameters including the difference, the gradient, the sum, the quotient, the function, the first or following differentiation and/or the like. For example the difference or the quotient may be a measure for the contrast. The gradient for example may be determined such that the parameters are determined based on the predetermined criterion i.e. are put in relation to specified criteria.

It is preferred that the detector determines at least the intensity and/or the wavelength of the incident radiation. A determination of the individual intensities allows conclusion of a light/dark contrast of the radiation impinging on the detector. A determination of the wavelength of the incident radiation or also individual wavelength ranges allows determining the color contrast.

It is preferred that only a specified wavelength or a predetermined wavelength range is used for averaging. It is further preferred that only a specified radiation intensity or a predetermined radiation intensity range is used for averaging.

It is further preferred for averaging to neglect individual signals whose intensity and/or wavelength lie outside a specified range. In this way, smoothed measurement results can be obtained.

It is preferred to compute an evaluation figure as a statistical quantity which is selected from a group of statistical quantities including arithmetic mean values, constant mean values, vectorial mean values, geometrical mean values, Fourier transforms, in particular but not exclusively Fourier sine and Fourier cosine transforms. It is preferred to average the mean value as a statistically floating mean value.

It is further preferred to select the statistical parameter from a group of parameters including the variance, the standard deviation, the diffusion, minima, maxima, the range and the like. These are preferably but not exclusively the variance of the individual radiation intensities captured or the variance of the captured wavelengths of the detected radiation.

The invention further relates to a device for employing the method of the invention for determining the properties of surfaces. The device comprises at least a first radiation means which projects or emits radiation to a measuring surface. Additionally, a detector means is provided which is positioned at a predetermined angle relative the measuring surface such that the radiation reflected and/or scattered off the measuring surface is at least partially incident on the detector means, said detector means comprising a plurality of image-capturing components wherein each image-capturing component emits a first signal characteristic of at least one parameter of the radiation incident on said image-capturing component.

At least one processor means is provided which groups the first signals of at least three image-capturing components to form a plurality of second group signals.

Said image-capturing components are elements or components which detect a captured image or captured radiation and emits a measuring signal characteristic of said radiation. These may for example be components whose resistance and/or current and/or charge changes in dependence on the intensity of the incident radiation.

It is preferred that each image-capturing component from the group of image-capturing components whose first signals are grouped to form a group signal, are adjacent to at least one other image-capturing component in said group.

This means that it is not signals of randomly arranged image-capturing components which are grouped but only the signals from such image-capturing components which at least in part are adjacent to one another or have a specified distance to one another.

Another preferred embodiment provides for the plurality of all of the image-capturing components to be arranged in an array which is at least one-dimensional, preferably at least two-dimensional. It is, however, also conceivable to provide a three-dimensional array wherein the image-capturing components in such a three-dimensional array may for example be positioned on a curved surface.

In addition, one single image-capturing component or also a plurality of image-capturing components may be provided which move in a specified, preferable one- or two-dimensional range.

It is preferred that the image-capturing components in at least one group of image-capturing components whose signals are grouped to form a group signal, are positioned in a sub-array which is at least one-dimensional. This means that the individual image-capturing components whose signals are grouped to form a group signal, are for example arranged in a 2×2, 3×3 etc. matrix. In another embodiment the image-capturing components whose first signals are grouped to form a group signal, may also be arranged along a line. In addition, non-quadratic arrays such as 1×4, 3×5 or 3×8 sub-arrays may also be formed.

In another embodiment the radiation means comprises at least one first radiation source from a group of radiation sources including light bulbs, light-emitting diodes, lasers, thermal radiation sources and the like. The light emitting from the radiation means may be diffused light or collimated light wherein diffused light may for example be generated by means of a diffusor disk.

In another preferred embodiment the radiation means comprises at least one radiation localizing component. This radiation localizing component is selected from a group of components including diaphragms, in particular but not exclusively, apertured diaphragms, grates, cut-off filters and the like.

In another preferred embodiment at least one radiation source is variable in at least one optical characteristic such as in-particular but not exclusively wavelength, polarization, intensity, modulation or the like. Modulation is understood to mean that the radiation source can be switched on and off or changed in intensity and/or another characteristic, at variable intervals.

In another preferred embodiment the radiation means comprises at least one radiation director means. This radiation director component is selected from a group of radiation director components including lenses, reflectors, such as in particular but not exclusively, parabolic reflectors and the like.

The first and/or second radiation director means may furthermore be selected from a group of devices including in addition to the lenses mentioned above, transmission and reflection grates, birefringent materials and the like.

In another preferred embodiment the radiation detector means comprises at least one dispersive component, i.e. a component having wavelength- or frequency-selective properties. However, said dispersive component does not have to be integrated in the radiation detector means but may be positioned at another place in the optical path between the measuring surface and the radiation detector means. A monochromator may be used additionally for examining or selecting the wavelength of light reflected or scattered off the measuring surface.

In another preferred embodiment, a second radiation director means is arranged between the measuring surface and the radiation detector means. It is preferred that the position of the first and/or the second radiation director means relative the measuring surface is variable.

In another preferred embodiment, the specified angle between the measuring surface and the radiation detector means is variable between 0° and 90°, preferred between 40° and 90° and particularly preferred between 80° and 90°.

In another preferred embodiment the device comprises a lens system which is preferably positioned between the measuring surface and the detector means.

The invention further relates to the application of the method described above and of the device for evaluating or determining the properties of surfaces in particular in the field of motor vehicles.

BRIEF DESCRIPTION OF THE DRAWINGS

Further advantages of the method of the invention and the device of the invention can be taken from the accompanying drawings.

FIGS. 5a–5c area schematic illustrations demonstrating the different resolution capabilities, for example, of the human eye.

DETAILED DESCRIPTION

Figure 1:
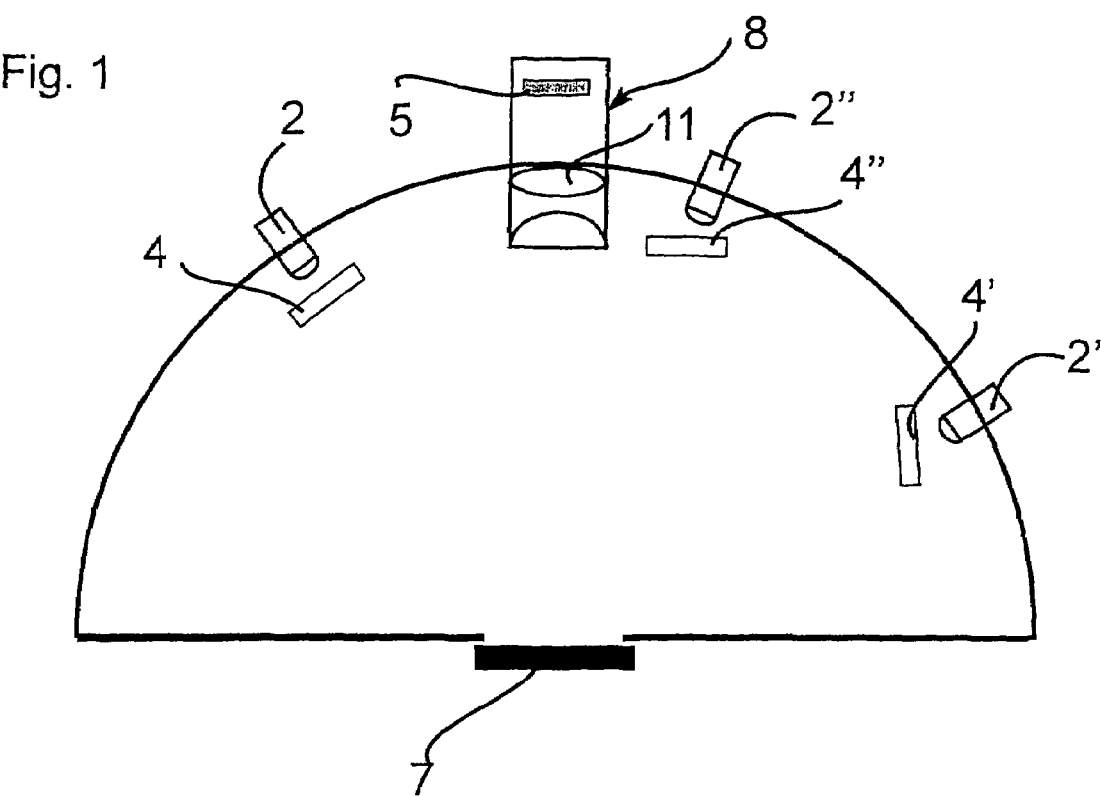
FIG. 1 illustrates a the device of the invention for determining the properties of surfaces.

FIG. 1 shows a first embodiment of the device of the invention for determining the properties of surfaces.

Reference numeral 2 refers to a radiation means. This embodiment comprises several radiation means 2 which are preferably evenly distributed in a space above the measuring surface 7.

Although FIG. 1 illustrates this space as a semicircle or a hemisphere, it may be of any other desired geometrical shape, for example a rectangle or the like.

Reference numeral 8 designates a radiation detector means comprising a radiation director means, i.e. a lens 11 and a plurality of image-capturing components arranged in an array 5. In addition, the radiation detector means may also comprise radiation localizing means (not shown) such as diaphragms, dispersive components, such as grates, frequency-dependent filters and the like.

The array with said plurality of image-capturing components is connected to an evaluation unit (not shown).

The individual radiation means may comprise radiation sources emitting light of different wavelengths; however, these may also be radiation sources emitting light of uniform wavelength.

Reference numeral 4 designates a diffusor means that diffuses the light emitting from the radiation means 2. Said diffusor means, as shown with the diffusor means 4', may be rotated or tilted relative a geometrical axis extending from the radiation means to the measuring surface.

Figure 2:
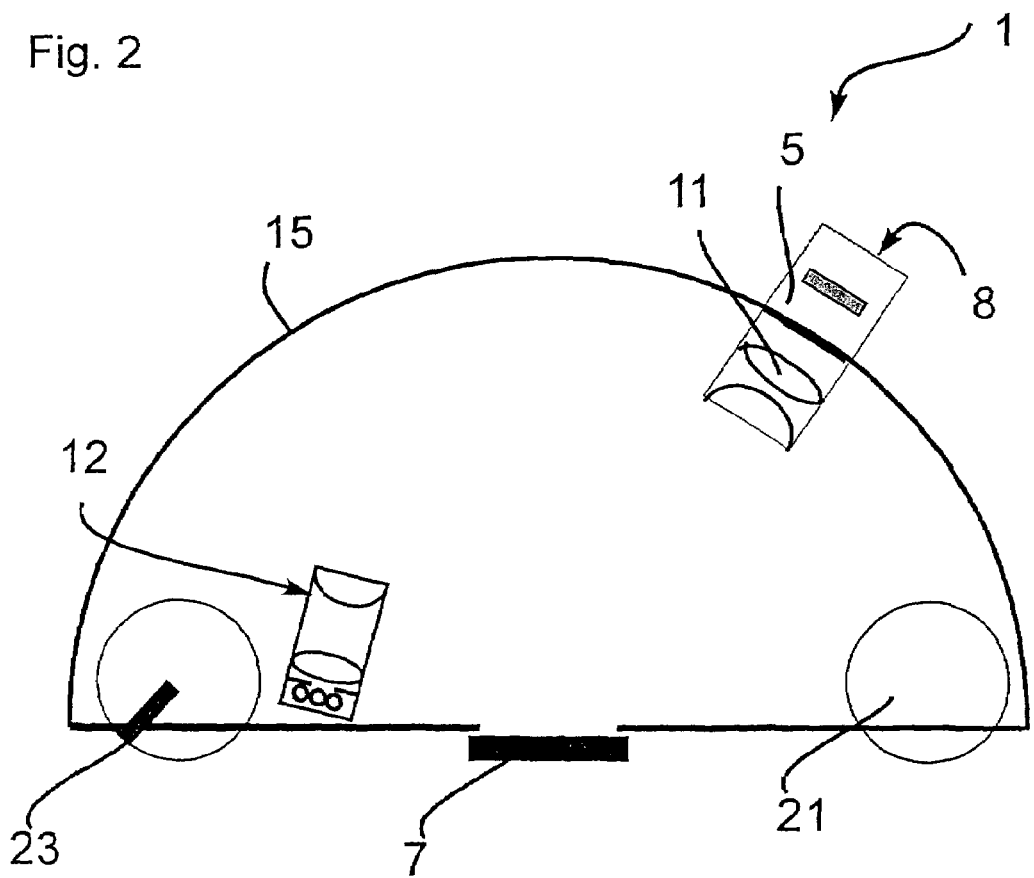
FIG. 2 illustrates a device of the invention for determining the properties of surfaces in another embodiment.

FIG. 2 shows another embodiment of the device of the invention for determining the properties of surfaces. The radiation detector means 8 in this embodiment is not positioned perpendicular to the measuring surface 7 but at a different angle.

Additionally, instead of several radiation means 2, only one radiation means 12 is provided. The light emitting from said radiation means 12 is preferably repeatedly reflected or scattered off the device housing 15 such that finally a portion of the reflected and/or scattered light will be incident on the measuring surface 7 and from there on the detector 8.

The housing 15 preferably has surfaces of reflecting and/or diffusing material, at least at the interior i.e. on the measuring surface 7 side. Another embodiment provides for the device to be movable relative the measuring surface which is indicated by the wheels 21. A travel measurement means 23 may be provided additionally which measures the distances traveled relative the measuring surface 7. It is preferred to design the device such that no outside light can enter, except such light as scattered and/or reflected off the measuring surface 7. In another preferred embodiment, a coating-thickness measurement means (not shown) may be provided which serves to determine the thickness, of the measuring surface. Said coating-thickness measurement means is preferably in physical contact with the measuring surface.

Figure 3:
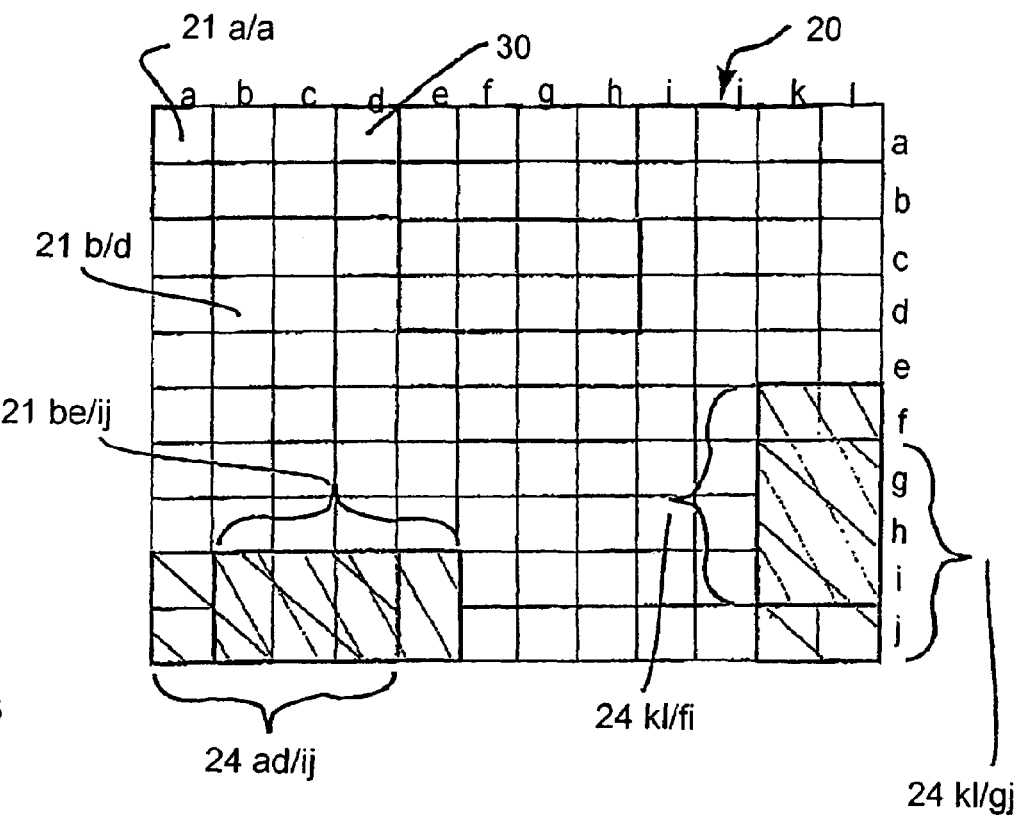
FIG. 3 is a schematic illustration of a plurality of image-capturing components arranged in an array.

FIG. 3 shows a plurality of image-capturing components arranged in an array 20.

Reference numeral 20 refers to the entire array with the individual image-capturing components. This array may be quadratic in shape, i.e. having the same numbers of rows and columns. However, the number of rows and columns may also differ.

The reference numerals 21 designate the individual image-capturing components, which are designated with letters such that the image-capturing component on the top left is designated with 21aa, the next one to the right with 21ab, etc.

When grouping individual signals to form a group signal, for examples, the signals from the image-capturing components 21ai, 21bi, 21ci, 21di, 21aj, 21bj, 21cj, 21djare grouped to form one signal designated with 24ad/ij. These first signals may be formed into a group signal, which, for example, may be the mean value of the individual signals. Individual first signals may be weighted higher than others so as to obtain a more strongly contrasting image. However, instead of the mean value other evaluation figures such as Fourier transforms may be formed as well.

FIG. 3 is an illustration of several mean values being formed such as in this case 24ad/ij, 24be/ij,24kl/fi, 24kl/gj, etc. This means that this is so-called floating averaging.

In a further step, a statistical parameter may be read out for example dependent on said mean value such as a variance or diffusion of the individual first signals or the like. Said statistical parameter will then be read out based on the respective criterion, i.e. for example relative the predetermined number of first signals. It is also preferred to again group the mean values formed, such as 24ad/ij, 24be/ij etc., to form another group signal. In this way, existing contrasts can be amplified because repeated counting results in individual signals to be weighted higher.

Before floating mean values are formed, it is preferred to group individual signals to form a group signal, as indicated by the rectangle 30. This serves to influence the resolution of the image reproduced by the array. The result, i.e. the corresponding resolution can be read out as a predetermined criterion for grouping the first signals.

Another modification of the method is to group the first signals to form a specified number of group signals and to evaluate these group signals by means of fast Fourier transform (FFT) so as to reduce the computing processes involved. In doing this, the group signals formed by grouping the first signals are transformed from position space to frequency space by Fourier transformation.

This method of operation in the position space generally includes that the pixel values, i.e. the first signals from the image-capturing components are directly manipulated in the imaging area and transformed into the image by means of discrete Fourier transformation (DFT)

Figure 4:
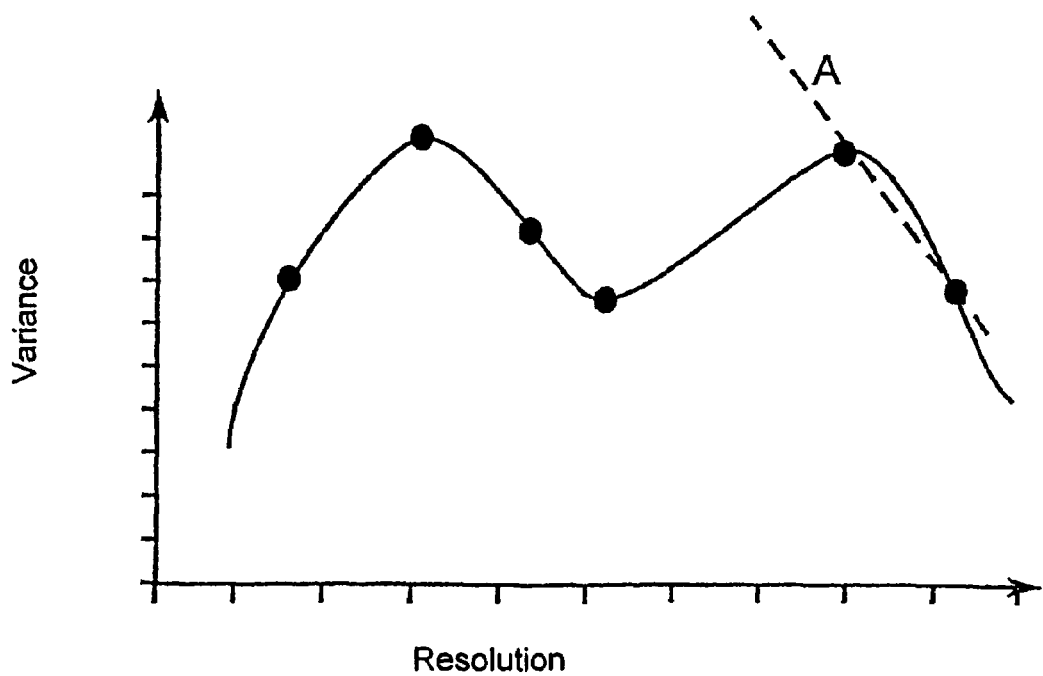
FIG. 4 is a diagram with a statistical parameter plotted on top of a specified criterion.

FIG. 4 shows an exemplary diagram with a statistical parameter plotted on top of a specified criterion. Said specified criterion is the resolution of the signal which substantially depends on the number of the first signals grouped to form the respective group signals.

The statistical parameter is the variance or diffusion of the first signals grouped to form the respective individual groups. In addition to the individual values for the statistical parameter, the gradient and generally any desired differentiations of the function represented by the continuous line may be read out so as to determine the path of the statistical parameter dependent on said predetermined criterion. In addition, the gradient between two discrete points may also be determined as indicated by the line A in FIG. 4.

FIGS. 5a–5c are simplified, schematic views of exemplary moiré patterns showing that periodic irregularities are recognizable, dependent on the resolution capability or the distance of the observer from the observed object. While FIG. 5a actually does not show any periodically repeated regularities, FIG. 5b already shows first indications of so-called moiré patterns.

The illustration 5c already shows clearly recognizable patterns.

Substantially random or non-recurring irregularities on the observed measuring surface also follow this principle.

The invention claimed is:

1. A method for determining the properties of surfaces including the following steps:
   emitting specified radiation from at least one radiation means to a measuring surface;
   detecting the emitted radiation that is reflected and/or scattered off the measuring surface by means of a detector means having a plurality of image-capturing components;
   generating first signals which specify at least one parameter of the radiation detected by the image-capturing components;
   grouping the first signals to form at least two group signals based on at least two different predetermined criteria;
   computing at least one group-specific evaluation figure and at least one statistical parameter dependent thereon which correlates with at least one remission characteristic of the measuring surface;
   reading out the at least one statistical parameter in dependence on the predetermined criterion for grouping said first signals;
   wherein the properties of the surface are specified by means of a relation between at least two statistical parameters based on different criteria.

2. The method according to claim 1,
   wherein for grouping said first signals to form a group signal, at least one of said first signals is weighted differently from at least another of said first signals.

3. The method of claim 1, wherein
   the criteria applied for grouping the first signals to form a group signal differ substantially in the number and/or the weighting and/or the function of the grouped first signals.

4. The method of claim 1, wherein
   the relation of the at least two parameters is selected from a group of parameters including the difference, the gradient, the sum, the quotient, the function, the nth differentiation and/or the like.

5. The method of claim 1, wherein
   the detector determines at least one parameter, in particular the wavelength and/or the intensity of the incident radiation.

6. The method of claim 1, wherein
   only a specified wavelength or a predetermined wavelength range is used for averaging.

7. The method of claim 1, wherein
   substantially only a predetermined radiation intensity range or intensity window is used for averaging.

8. The method according to claim 1, wherein
   the at least one group-specific evaluation figure is computed as the mean value selected from a group of statistical quantities including arithmetic mean values, floating mean values, vectorial mean values, geometrical mean values, and harmonic mean values.

9. The method of claim 1, wherein
   the mean value is averaged as a statistically floating mean value.

10. The method according to claim 1, wherein the at least one statistical parameter is selected from a group of parameters including the variance, the standard deviation, the diffusion, maxima, minima, and the range.

11. A device for carrying out the method for determining the properties of surfaces according to claim 1 comprising:
    at least one radiation means projecting radiation onto a measuring surface;
    at least one detector means which is positioned at a predetermined angle relative the measuring surface such that the radiation reflected and/or scattered off the measuring surface is at least partially incident on the detector means, said detector means comprising a plurality of image-capturing components wherein each image-capturing component emits at least one of said first signals which is characteristic of at least one parameter of the radiation incident on the allocated image-capturing component,
    wherein at least one processor means is provided which groups the first signals of at least two image-capturing components to form a plurality of group signals.

12. The device according to claim 11,
    wherein each image-capturing component from the group of image-capturing components whose first signals are grouped to form a group signal, are adjacent to at least one other image-capturing component in said group.

13. The device according to at claim 11, wherein
    the plurality of image-capturing components is arranged in at least one array that is at least one-dimensional.

14. The device according to claim 11, wherein
    the image-capturing components from at least one group of image-capturing components whose first signals are grouped to form a group signal, are positioned in at least one sub-array, and wherein said at least one sub-array is at least a one-dimensional sub-array.

15. The device in particular according to claim 11, wherein
    the radiation means comprises at least one radiation source from a group of radiation sources including light bulbs, light-emitting diodes, lasers, thermal radiation sources and the like.

16. The device in particular according to claim 15, wherein
    at least one radiation source is variable in at least one optical characteristic such as in particular but not exclusively wavelength, polarization, intensity, modulation or the like.

17. The device in particular according to claim 11, wherein
    the radiation means comprises at least one radiation localizing component.

18. The device in particular according to claim 17, wherein
    the radiation localizing component is selected from a group of components including diaphragms, in particular but not exclusively, apertured diaphragms, grates, cut-off filters and the like.

19. The device in particular according to claim 11, wherein
the radiation means comprises at least one first radiation director means.

20. The device in particular according to claim 19, wherein
a second radiation director means is arranged between the measuring surface and the detector means.

21. The device in particular according to claim 20, wherein
the position of the first and/or the second radiation director means relative the measuring surface is variable.

22. The device in particular according to claim 20, wherein
at least one of the first and the second radiation director means is selected from a group of devices including lenses, transmission and reflection grates, prisms, birefringent materials and the like.

23. The device in particular according to claim 20, wherein
an optical axis of the second radiation director means is arranged at a second specified angle relative an array of the plurality of image-capturing components.

24. The device in particular according to claim 23, wherein
said second specified angle is between 0 degrees and 90 degrees, preferred between 30 degrees and 90 degrees and particularly preferred between 80 degrees and 90 degrees.

25. The device in particular according to claim 11, wherein
the detector means comprises at least one dispersive component.

26. The device in particular according to claim 11, wherein
the device comprises a lens system.

27. The device in particular according to claim 26, wherein
the lens system is positioned between the measuring surface and the detector means.

28. An application of the device of claim 11 for determining the properties of surfaces, in particular the properties of surfaces of motor vehicle finishes.

29. An application of the method of claim 1 for determining the properties of surfaces, in particular the properties of surfaces of motor vehicle finishes.

* * * * *